US011363979B2

(12) United States Patent
Dayeh et al.

(10) Patent No.: US 11,363,979 B2
(45) Date of Patent: Jun. 21, 2022

(54) ADDRESSABLE VERTICAL NANOWIRE PROBE ARRAYS AND FABRICATION METHODS

(71) Applicant: The Regents of the University of California, Oakland, CA (US)

(72) Inventors: Shadi A. Dayeh, San Diego, CA (US); Renjie Chen, Albuquerque, NM (US); Sang Heon Lee, La Jolla, CA (US); Ren Liu, La Jolla, CA (US); Yun Goo Ro, La Jolla, CA (US); Atsunori Tanaka, La Jolla, CA (US); Yoontae Hwang, Seoul (KR)

(73) Assignee: The Regents of the University of California, Oakland, CA (US)

( * ) Notice: Subject to any disclaimer, the term of this patent is extended or adjusted under 35 U.S.C. 154(b) by 1004 days.

(21) Appl. No.: 16/069,783

(22) PCT Filed: Jan. 19, 2017

(86) PCT No.: PCT/US2017/014143
§ 371 (c)(1),
(2) Date: Jul. 12, 2018

(87) PCT Pub. No.: WO2017/127551
PCT Pub. Date: Jul. 27, 2017

(65) Prior Publication Data
US 2019/0021619 A1    Jan. 24, 2019

Related U.S. Application Data

(60) Provisional application No. 62/280,366, filed on Jan. 19, 2016.

(51) Int. Cl.
*A61B 5/24*        (2021.01)
*B81B 1/00*        (2006.01)
(Continued)

(52) U.S. Cl.
CPC ............ *A61B 5/24* (2021.01); *B81B 1/008* (2013.01); *B81C 1/00111* (2013.01);
(Continued)

(58) Field of Classification Search
CPC .. A61B 5/24; A61B 5/25; A61B 5/293; A61B 2562/0285; A61B 2562/046;
(Continued)

(56) References Cited

U.S. PATENT DOCUMENTS 7,905,013 B2 *   3/2011  Zhang ................... B82Y 30/00
                                                    29/853
7,991,475 B1     8/2011  Tang et al.
(Continued)

OTHER PUBLICATIONS

Chen et al., "Size and Orientation Effects on the Kinetics and Structure of Nickelide Contacts to InGaAs Fin Structures", Nano Letters, vol. 15, pp. 3770-3779, 2015.
(Continued)

*Primary Examiner* — Eun Hwa Kim
(74) *Attorney, Agent, or Firm* — Greer, Burns & Crain, Ltd.; Steven P. Fallon

(57) ABSTRACT

A nanowire probe sensor array including a substrate with a metal pattern thereon. An array of semiconductor vertical nanowire probes extends away from the substrate, and at least some of probes, and preferably all, are individually electrically addressed through the metal pattern. The metal pattern is insulated with dielectric, and base and stem portions of the nanowires are also preferably insulated. A fabrication process patterns metal connections on a substrate. A semiconductor substrate is bonded to the metal pattern. The semiconductor substrate is etched to form the neural nanowire probes that are bonded to the metal pattern. Dielectric is then deposited to insulate the metal pattern.

20 Claims, 14 Drawing Sheets

(51) Int. Cl.
*B81C 1/00* (2006.01)
*G01N 33/483* (2006.01)
*B82Y 15/00* (2011.01)

(52) U.S. Cl.
CPC .......... *B82Y 15/00* (2013.01); *G01N 33/4836* (2013.01); *A61B 2562/0209* (2013.01); *A61B 2562/0285* (2013.01); *A61B 2562/046* (2013.01); *A61B 2562/125* (2013.01); *B81B 2201/055* (2013.01); *B81C 2201/016* (2013.01); *B81C 2201/0132* (2013.01); *B81C 2203/035* (2013.01)

(58) Field of Classification Search
CPC ..... B81B 1/008; B81C 1/00111; B82Y 15/00; G01N 33/4836
See application file for complete search history.

(56) References Cited

U.S. PATENT DOCUMENTS

| | | | |
|---|---|---|---|
| 9,283,386 B2* | 3/2016 | Park | A61B 5/6877 |
| 2003/0189202 A1 | 10/2003 | Li et al. | |
| 2008/0090401 A1* | 4/2008 | Bratkovski | H01Q 15/0006 |
| | | | 438/597 |
| 2010/0176822 A1* | 7/2010 | Offermans | H01L 29/0676 |
| | | | 977/762 |
| 2012/0153124 A1 | 6/2012 | Yu et al. | |
| 2013/0284612 A1* | 10/2013 | Park | B82Y 5/00 |
| | | | 205/792 |
| 2014/0128972 A1 | 5/2014 | Khraiche et al. | |
| 2015/0126843 A1 | 5/2015 | Pemba et al. | |
| 2016/0128588 A1* | 5/2016 | Melosh | A61N 1/0534 |
| | | | 600/378 |

OTHER PUBLICATIONS

Dai et al., "Novel Heterogeneous Integration Technology of III-V Layers and InGaAs FinFETs to Silicon", Advanced Functional Materials, vol. 24, pp. 4420-4426, 2014.
Duan et al., "Intracellular recordings of action potentials by an extracellular nanoscale field-effect transistor", Nat. Nanotechnol., vol. 7, No. 3, pp. 174-179, 2012.
Hai et al., "In-cell Recordings by Extracellular Microelectrodes", Nature Methods, vol. 7, No. 3, pp. 200-203, Mar. 2010.
Hanson et al., "Characterization of the Cell-Nanopillar Interface by Transmission Electron Microscopy", Nano Letters, vol. 12, pp. 5815-5820, Oct. 3, 2012.
Kim et al., "Interfacing Silicon Nanowires with Mammalian Cells", J. Am. Chem. Soc., vol. 129, pp. 7228-7229, 2007.
Lin et al., "Iridium oxide nanotube electrodes for sensitive and prolonged intracellular measurement of action potentials", Nature Communications, vol. 5, 3206, 2014.
Merz et al., "Silicon chip interfaced with a geometrically defined net of snail neurons", Advanced Functional Materials, vol. 15, No. 5, pp. 739-744, 2005.
Neher et al., "Single-channel currents recorded from membrane of denervated frog muscle fibres", Nature, vol. 260, 5554, pp. 799-802, Apr. 29, 1976.
Piret et al., "Neurite Outgrowth and Synaptophysin Expression of Postnatal CNS Neurons on GaP Nanowire Arrays in Long-Term Retinal Cell Culture," Biomaterials, vol. 34, pp. 875-887, 2013.
Robinson et al., "Vertical nanowire electrode arrays as a scalable platform for intracellular interfacing to neuronal circuits", Nat. Nanotechnol., vol. 7, No. 3, pp. 180-184, 2014.
Wang et al., "Neural stimulation with a carbon nanotube microelectrode array", Nano letters, vol. 6, No. 9, pp. 2043-2048, 2006.
Wise, "Silicon microsystems for neuroscience and neural prostheses". Engineering in Medicine and Biology Magazine, vol. 24, No. 5, pp. 22-29, IEEE 2005.
Xie et al., "Intracellular Recording of Action Potentials by Nanopillar Electroporation", Nat. Nanotechnol., vol. 7, No. 3, pp. 185-190, 2012.
Thomas, Shane, International Search Report for Application No. PCT/US2017/014143, dated May 25, 2017.

* cited by examiner

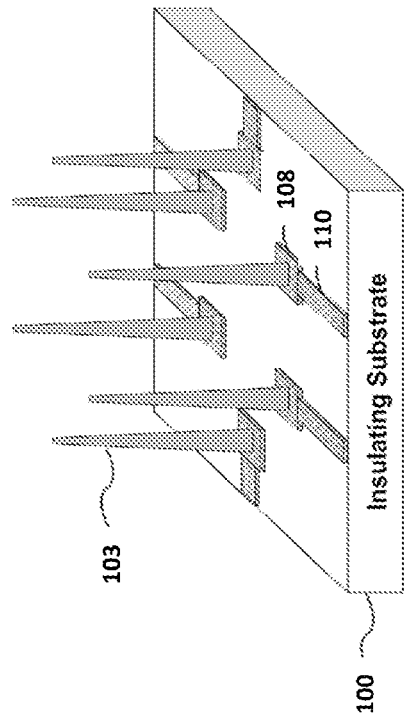
Figure 1B
Figure 1A
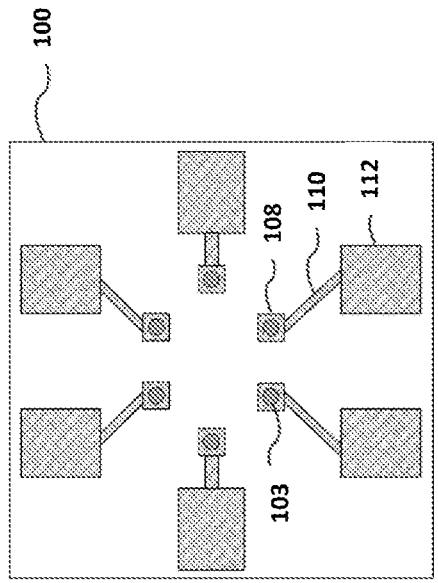
Figure 1C

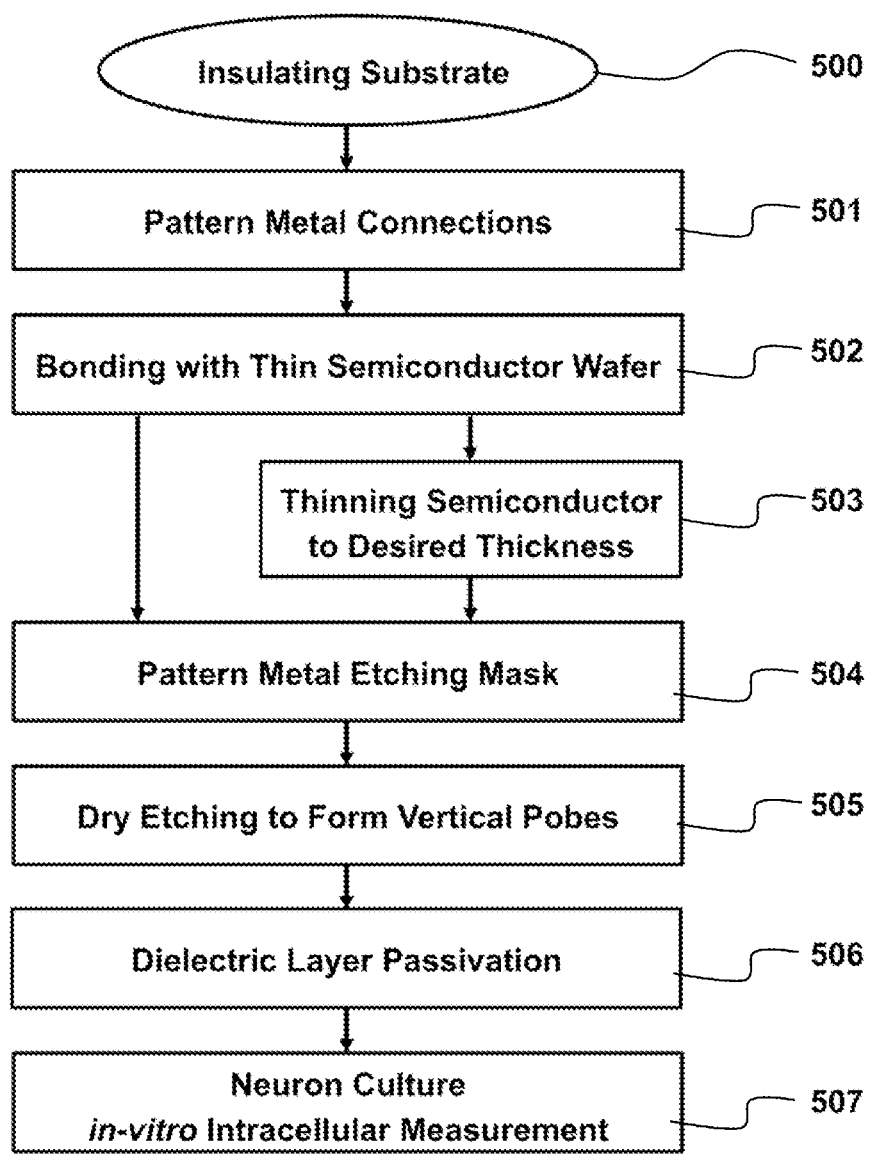

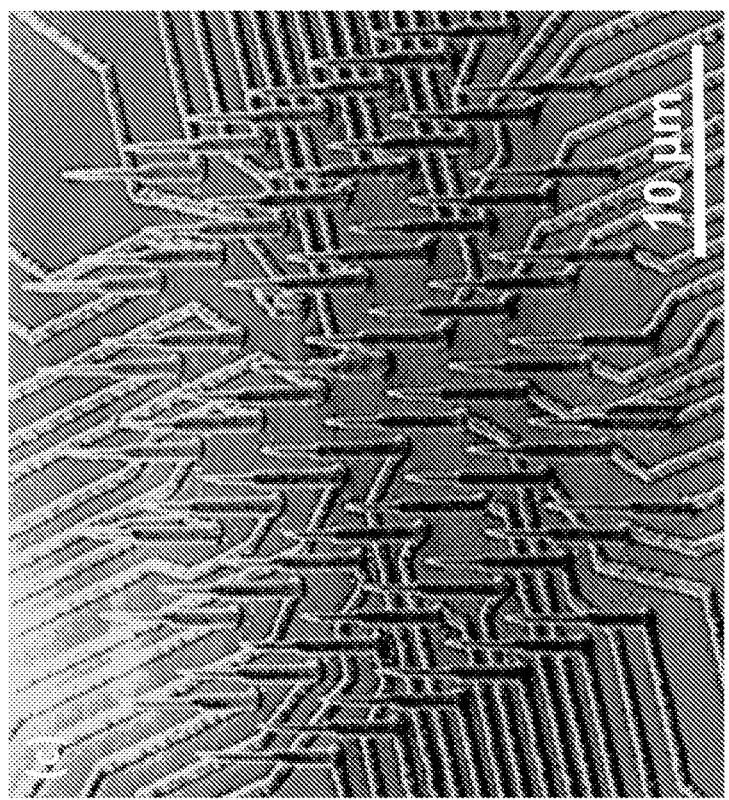
Figure 7C
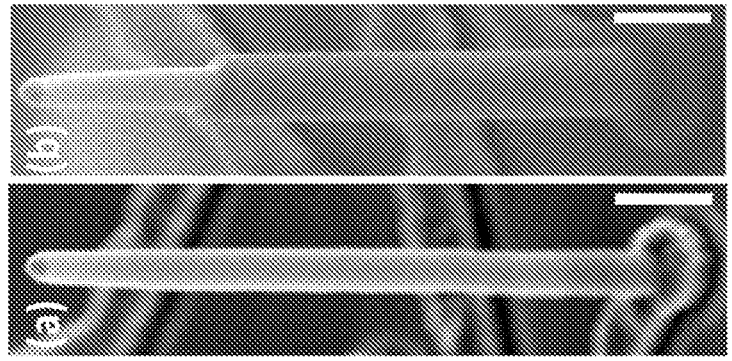
Figure 7B
Figure 7A

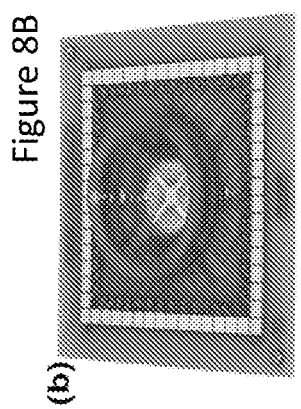
Figure 8A
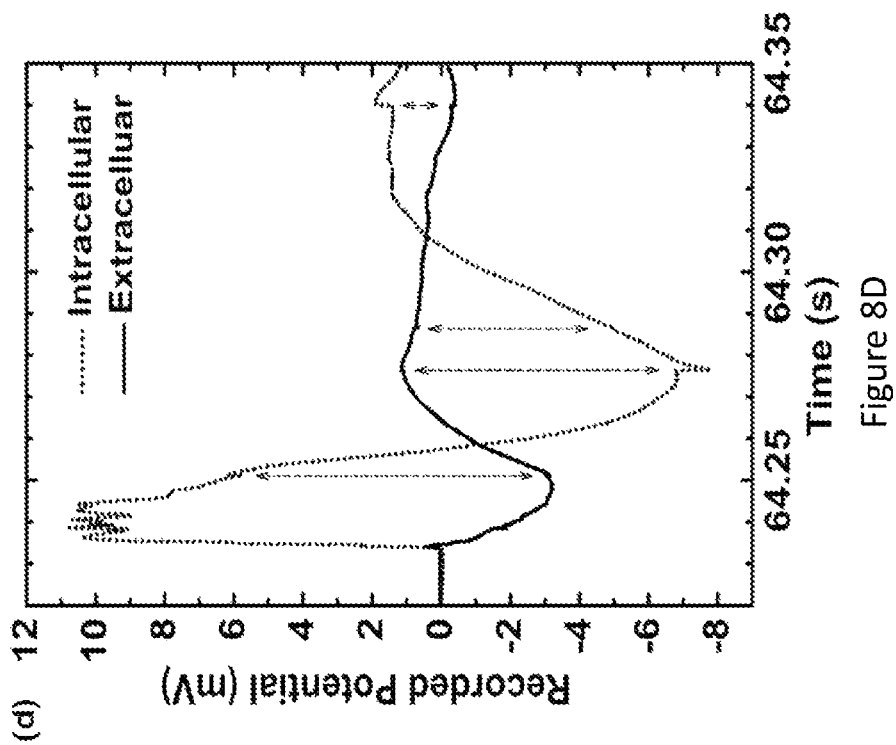
Figure 8B
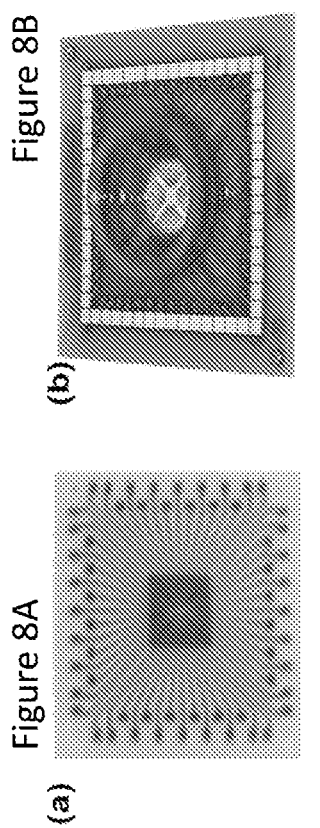
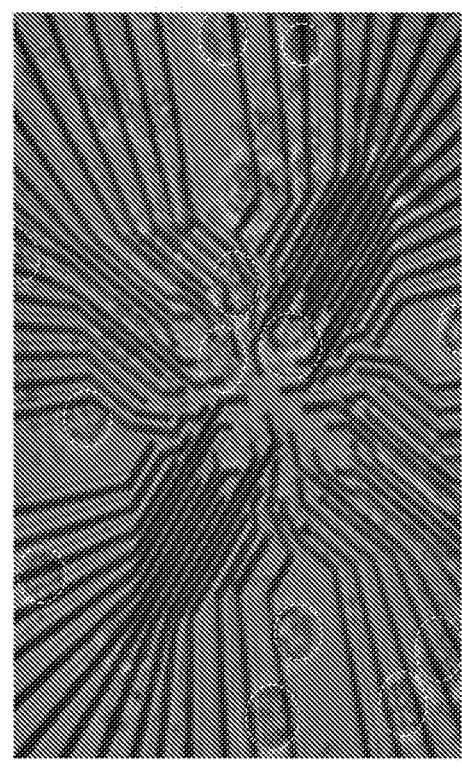
Figure 8C
Figure 8D

ADDRESSABLE VERTICAL NANOWIRE PROBE ARRAYS AND FABRICATION METHODS

PRIORITY CLAIM AND REFERENCE TO RELATED APPLICATION

The application claims priority under 35 U.S.C. § 119 and all applicable statutes and treaties from prior U.S. provisional application Ser. No. 62/280,366, which was filed Jan. 19, 2016.

FIELD

Fields of the invention include nanostructures, biological sensors, neural probes, cardiomyocyte probes, drug screening technologies, drug delivering technologies, and arrays of neural probes.

BACKGROUND

Uncovering minute details of the electrophysiological states of excitable cells, such as neurons in the brain or cardiomyocytes in the heart on an individual or network level can advance the understanding of the functional and diseased states of such organs and aid in developing rehabilitation technologies and medicine. The electrophysiological state of the cell is usually studied with sensitive probes that can have access to the interior (cytoplasm) of the cell, thereby enabling the sensitive measurements of the minute potential fluctuations of a single or multiple cells within a network of cells. These probes include patch-clamp with glass micropipette, microelectrode/nanoelectrode arrays (MEAs/NEAs), and nanowire (NW) filed effect transistor (FET), and with different materials, such as vertical nanowire arrays made of Si, Pt, and $IrO_x$.

Traditional glass micropipette electrodes with patch-clamp method [Neher, E.; Sakmann, B., Single-channel currents recorded from membrane of denervated frog muscle fibres. Nature 1976, 260 (5554), 799-802] are typically limited single channel measurements and at most less than about ten channels, with tedious and laborious alignment under the microscope, and the gigaseal between glass micropipette tip and the cell membrane is difficult to maintain longer than several hours. This technology provides the highest fidelity neural recordings of the examples in the previous paragraph, but it is not scalable to large number of probes. As a practical matter, a large number of probes is critical to the investigation of neuronal functionality. The patch-clamp techniques are also destructive to the cell being probed, and the "one-cell-at-a-time" approach also doesn't resemble the natural configuration of functioning cellular networks.

Benefiting from the development of planar microfabrication technologies, microelectrode arrays have evolved as standard platforms for studying electrophysiological responses from cellular networks over long durations (several weeks). However, planar microelectrode arrays cannot access the cellular cytoplasm and measure the minute potential changes inside the cell that provides a signature of its physiological state and activity. Such sensitivity, absent in microelectrode arrays, is critical to understand cellular function and to develop drugs with high throughput and efficacy.

Prior Si probes include Michigan probes [Wise, K. D., Silicon microsystems for neuroscience and neural prostheses. Engineering in Medicine and Biology Magazine, IEEE 2005, 24 (5), 22-29] and Utah electrode arrays [Normann, R. A., Technology insight: future neuroprosthetic therapies for disorders of the nervous system. Nature Clinical Practice Neurology 2007, 3 (8), 444-452], and Si NEAs [Robinson, J. T.; Jorgolli, M.; Shalek, A. K.; Yoon, M.-H.; Gertner, R. S.; Park, H., Vertical nanowire electrode arrays as a scalable platform for intracellular interfacing to neuronal circuits. Nature nanotechnology 2012, 7 (3), 180-184]. To the knowledge of the inventors, no such electrode arrays are fabricated with pitch below 1 µm and/or with individual electrode addressability, leaving the mapping of neural circuits with sub-cellular resolution still impossible, especially at the capacity of intra-cellular probing.

NEAs have been investigated with other bio-compatible materials, such as carbon nanotubes (CNTs) [Wang, K.; Fishman, H. A.; Dai, H.; Harris, J. S., Neural stimulation with a carbon nanotube microelectrode array. Nano letters 2006, 6 (9), 2043-2048] and IrOx [Zhang et al., U.S. Pat. No. 7,905,013: Method for forming an iridium oxide ($IrO_x$) nanowire neural sensor array]. Those NEAs were achieved with pre-defined contact leads on the substrate followed by selective growth of nanowires on the designed electrodes. This is a non-controlled process and does not have potential for scaling for multiple electrode sites. Example additional known NEAs include Si [Robinson, J. T.; Jorgolli, M.; Shalek, A. K.; Yoon, M.-H.; Gertner, R. S.; Park, H., Vertical nanowire electrode arrays as a scalable platform for intracellular interfacing to neuronal circuits. Nature nanotechnology 2012, 7 (3), 180-184], Pt [4. Xie, C.; Lin, Z.; Hanson, L.; Cui, Y.; Cui, B., Intracellular recording of action potentials by nanopillar electroporation. Nature nanotechnology 2012, 7 (3), 185-190], and IrOx [Lin, Z. C.; Xie, C.; Osakada, Y.; Cui, Y.; Cui, B., Iridium oxide nanotube electrodes for sensitive and prolonged intracellular measurement of action potentials. Nature communications 2014] nanowires. Such NEAs provided evidence that neuronal and cardiomyocyte cell activity can be measured with nanowire technologies. A highly sensitive microelectrode array is the Au-mushroom array [Hai, A.; Shappir, J.; Spira, M. E., In-cell Recordings by Extracellular Microelectrodes. Nature Methods 2010, 7, 200], but this is not scalable to dimensions that permit cell internalization.

In the example Zhang et al, U.S. Pat. No. 7,905,013, a dielectric layer over a conduct layer is selectively wet etched, forming contact holes with sloped walls in the dielectric layer and exposing regions of the conductive layer. IrOx nanowire neural interfaces are then grown from the exposed regions of the conductive layer. The IrOx nanowire neural interfaces each have a cross-section in a range of 0.5 to 10 micrometers, an average height in the range of about 10 nanometers (nm) to about 10 micrometers (µm), and an average proximal end diameter in a range of about 1 nm to about 1 µm. Zhang reports clusters of probes on chips ranging from 1 to 100 square millimeters. The clusters each include as few as 2 to as many as 12 electrodes, located within a cluster diameter in the range of 5 to 50 micrometers, where the number of clusters on the chip is in a range between 2 and 100.

Vertical nanowires possess many desirable attributes for probing neuronal networks. They permit the size necessary for permeation into neuron cell bodies and neurites with minimal invasiveness. See, e.g., W. Kim, J. K. Ng, M. E. Kunitake, B. R. Conklin, and P. Yang, "Interfacing Silicon Nanowires with Mammalian Cells," J. Am. Chem. Soc. 129, 7228, 2007; G. Piret, M. T. Perez, C. N. Pinz, "Neurite Outgrowth and Synaptophysin Expression of Postnatal CNS Neurons on GaP Nanowire Arrays in Long-Term Retinal Cell Culture," Biomaterials 34, 875, 2013; L. Hanson, Z. C.

Lin, C. Xie, Y. Cui, and B. Cui, "Characterization of the Cell-Nanopillar Interface by Transmission Electron Microscopy," *Nano Lett.* 12, 5815, 2012. This enables the measurement of high fidelity signals with high signal-to-noise ratios, more localized intervention with neurons, and, potentially, the recording of subthreshold activity. X. Duan, R. Gao, P. Xie, T. Cohen-Karni, Q. Qing, H. S. Choe, B. Tian, X. Jiang, and C. M. Lieber, "Intracellular Recordings of Action Potentials by an Extracellular Nanoscale Field-Effect Transistor," *Nano Lett.* 7, 174-179, 2012. Earlier work on single Si nanowires and nanotubes have demonstrated measurements of intracellular activity from single devices (Xie et al., supra) or devices constructed with arrays of electrically shorted or indistinguishable nanowires [J. T. Robinson, M. Jorgolli, A. K. Shalek, M.-H. Yoon, R. S. Gertner, and H. Park, "Vertical nanowire Electrode Arrays as Scalable Platform for Intracellular Interfacing to Neuronal Circuits," *Nature Nanotech.* 7, 180-184, 2012] and contributed to significant advances in electrophysiology.

None of the prior works using nanowire arrays have resulted in individually addressable nanowires. These include the Si NW arrays of Robnison et al, which were achieved with arrays of 9 nanowires per site with ~2 µm height, at a spacing of 190 µm between different arrays [Robinson et al., supra]. The Pt electrodes were fabricated with the serial focused ion beam deposition and were achieved with 5 nanowires per site, <2 µm height, and at a spacing of 100 µm between different arrays [Xie et al, supra]. The IrOx nanowire/nanotube arrays were fabricated by electrodeposition and achieved with arrays of 9 nanowires per site with <2 µm height [Lin et al, supra]. Additionally, all these short nanowires required electroporation, and the application of a high electric field to achieve breakdown of the cell membrane, in order for the nanowire/nanotube to penetrate the cells and measure the intracellular potentials.

SUMMARY OF THE INVENTION

A preferred embodiment of the invention is a neural probe sensor array including a substrate with a metal pattern thereon. An array of semiconductor vertical nanowire probes extends away from the substrate, and at least some of probes, and preferably all, are individually electrically addressed through the metal pattern. The metal pattern is insulated with dielectric, and base and stem portions of the nanowires are also preferably insulated.

Preferred methods of fabrication of the invention fabricate a neural probe sensor array by patterning metal connections on a substrate. A semiconductor substrate is bonded to the metal pattern. The semiconductor substrate is etched to form the neural nanowire probes that are bonded to the metal pattern. Dielectric is then deposited to insulate the metal pattern, and preferably the stems of the probes are also passivated with the dielectric material.

BRIEF DESCRIPTION OF THE DRAWINGS

FIGS. 1A to 1C are respective schematic cross-sectional, perspective (partial) and top views of a preferred embodiment neural probe sensor array in accordance with the invention;

FIG. 5 is a flowchart that illustrates the overall process flow of a preferred method for fabricating a neural probe sensor array in accordance with the invention;

FIGS. 7A-7C are SEM images of experimental steps demonstrating the passivating of example Si NEAs with $SiO_2$ coating; FIG. 7A shows a single Si nanowire on its metal contact; FIG. 7B shows the single Si nanowire after $SiO_2$ passivation with its tip exposed for neural signal recording and stimulation; and FIG. 7C shows a large experimental neural probe sensor array in accordance with the invention fabricated with Si vertical nanowires passivated with an $SiO_2$ layer;

FIG. 8A is a photography of an example neural probe sensor array in accordance with the invention with Ni electrodes on a sapphire substrate; FIG. 8B illustrate the array bonded to a PCB (printed circuit board) stage with conductive epoxy, which allows the peripheral 64 electrodes to be connected to an analysis system, such as System 3® from Tucker-Davis Technologies; FIG. 8C is a microscope image of cultured pyramidal neurons from CA1 and CA3 of mouse hippocampus on the FIG. 8B chip with sensor array; and FIG. 8D is data of recorded potentials from typical experimental neural probe sensor arrays of the invention showing positive (top) and negative (bottom) signals at the same time measured at separate electrodes, indicating potentially intra-(top) and extra-(bottom) cellular recording;

DETAILED DESCRIPTION OF THE PREFERRED EMBODIMENTS

Figure 2A:
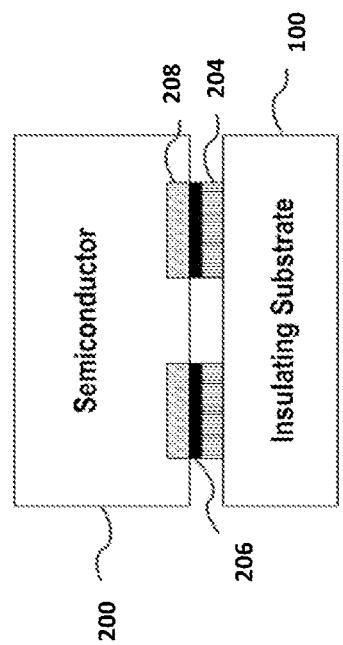
FIGS. 2A and 2B are schematic cross-sectional views of sequential steps for bonding a semiconductor material on a substrate in a preferred method for fabricating a neural probe sensor array in accordance with the invention.

A preferred embodiment of the invention is a neural probe sensor array including a substrate with patterned and addressable metal contacts thereon. An array of semiconductor penetrating vertical nanowires are electrically addressed through the addressable metal contacts and extend away from the substrate. The addressable metal contacts are insulated, and stem portions of the nanowires are also preferably insulated.

Preferred methods of fabrication of the invention fabricate a neural probe sensor array by patterning metal connections on a substrate. A semiconductor substrate is bonded to the metal pattern. The semiconductor substrate is etched to form the neural probes that are bonded to the metal pattern. Dielectric is then deposited to insulate the metal pattern, and preferably the stems of the probes are also passivated with the dielectric material.

Such preferred fabrication methods of the invention are capable of producing high-density arrays of very thin diameter neural probes in various patterns. High density neural probe arrays can be fabricated with individual addressability. In use, the arrays can provide large scale neural mapping with sub-cellular resolution, detect intracellular signal with less damage to the neuronal cells, and have enough mechanical strength to be tolerant of cell micro motions. Fabrication methods of the invention can produce neural probe arrays and are scalable to several thousands and tens of thousands of electrode sites.

Preferred embodiment neural probe arrays provide unique architectures that enable intracellular neural probing (recording and stimulation) at very high densities for in vitro neuronal networks. While not bound to the theory and not being necessary to demonstrate the advance provided by the invention, the inventors believe that preferred arrays of the invention with individual addressability of vertical penetrating Si electrode arrays (that can be coated with metallic or dielectric coatings, for example) provide neural probe arrays with unprecedented high density. Arrays of the invention provide such density while being fabricated on substrate and conducted through underneath metal leads. Preferred nanowires in nanowire arrays of the invention can be coated with dielectric, or with conductive materials. Example coatings include silicon dioxide, AgCl, and Pt. In preferred fabrication methods, the nanowire array is coated with dielectric, then the tips of the nanowires are exposed (e.g., about ⅓ the length), and the tips can be coated with another material, In preferred embodiments, integration of a biocompatible semiconductor material, e.g. Si, onto an insulating substrate, e.g. sapphire, is achieved by a wafer bonding process through a solid-state reaction between semiconductor and metal leads that are patterned on the insulating substrate. Those metal leads serve as both the selective bonding layers during the fabrication process and the conducting electrode leads in the finished neural probe array. A preferred alignment procedure defines and patterns an etching mask on the semiconductor layer by e-beam lithography (EBL), and the semiconductor electrode arrays are formed via a dry etching process and perfectly aligned to predetermined portions of the metal leads on the substrate, e.g., on predetermined end portions of one or more lead lines. Generally, preferred methods are substrate independent for substrates that tolerate temperatures in the range of ~300-400° C. Prior common wafer bonding techniques uses eutectic techniques. In the context of fabricating nanowire arrays, such techniques would cause electrodes to melt and merge with each other.

Fabrication methods of the invention are CMOS compatible and can provide a large variety of geometrical designs of the leads and penetrating electrodes that facilitate spatial mapping of neuronal networks with high resolution. Great layout flexibility is provided by preferred fabrication methods that combine photolithography, EBL, wafer bonding, dry etching, and wet chemical processes.

Prototypes have been fabricated to demonstrate high density vertical semiconductor nanowire arrays (NEAs) on insulating substrates for intracellular neural probes with individual electrode addressability. Compared with existing neural and cardiomyocyte neural probe devices, our invention shows a number of merits that include:

Sub-cellular spatial resolution in neuronal signal recording and stimulating: preferred fabrication methods enables the fabrication of Si neural probe arrays with nanometer scale size and pitch, which is suitable to record, inhibit, or stimulate or caryiomyocyte activities at single or network levels. Present experimental arrays have been fabricated with individual probes smaller than 200 nm in diameter and the pitch as small as 750 nm in linear arrays and as small as 4 μm spacing between independent vertical nanowires in square arrays. These ultra-scaled and highly compacted NEAs enable recording of potential fluctuations and action potential generation and propagation.

High fidelity of signals and high efficiency of stimulation. The vertical nanowire probe electrodes can contain tall (~10 μm) vertical Si nanowire probes that can penetrate through the cell membrane and detect intracellular signals. Intracellular recording measure the voltage/current across the cell membrane, with signals that can be as large as several tens of millivolts, while extracellular signals are typically <10 mV which compares to usually less than 1 mV for planar microelectrode arrays. The tighter interaction between the cell and nanowire provides excellent coupling of the cell activity to the nanowire and therefore result in higher signal-to-noise ratio, and better tolerance to the high impedance of electrodes that are associated with the smaller nanowire surface area than the planar microelectrode arrays.

Stable interfacing with neuron cells. On the one hand, the reduced size of electrodes mitigates the mechanical mismatch with cells, improving the potential for long-term interfacing with neuron or cardiomyocyte cells. One the other hand, the Si wafer is bonded to sapphire wafer through the solid-state reaction between Si and Ni electrodes, and the Si/NiSi interface provides enough strength and adhesion for the NEAs, which enhances the device stability by ruling out the delamination failures.

Flexibility of layout. Preferred fabrication methods allow arranging the vertical penetrating electrodes insulated leads with various patterns, densities and locations, which can be tailored according to different electrophysiological measurement goals and requirements. As an example, neurons have been proven to have stable patterns in orthogonally or hexagonally intersecting paths [Merz, M.; Fromherz, P., Silicon chip interfaced with a geometrically defined net of snail neurons. *Advanced Functional Materials* 2005, 15 (5), 739-744], and preferred neural probe arrays of the invention accordingly are patterned to map the interaction between neurons in a large network of neurons.

CMOS compatibility. A very important aspect of the present fabrication processes is the nanowire arrays can be integrated directly on top of amplifier, digitization and acquisition and other integrated circuits because the present fabrication processes can be performed at temperatures consistent with maintain the integrity of the already formed CMOS integration. This provides a potential for high throughput manufacturing that together with the high sensitivity can provide significant performance gains in electrophysiology platforms, particularly for drug screening technologies.

Neural probe arrays of the invention can replace conventional planar or 3D microelectrode arrays. Intracellular capability at high densities allows for precise measurement of neuronal activity and the minute potential fluctuations that precedes such activity. The applications can extend to longer NEAs for retinal studies and brain-slice measurements. The nanoscale 3D aspects will can enable studies and development of new frontiers in neurosciences and may impact our understanding of how neurons interact together in a neuronal network.

An important application of the invention is in drug screening. Initial measurements on human stem cell derived neurons have shown that such cells can grow for and interface with neurons in the intracellular configuration for 6 weeks after culture and that they were response to pharmacological stimulation and inhibition (see additional details following claims). The ability to measure small potential fluctuations due to drug addiction from nanowires as opposed to aligning a patch-clamp under a microscope allows scaling the platform for rapid and efficient screening of drugs for neurodegenerative, cardiac, and other diseases Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

FIGS. 1A-1C illustrate a preferred embodiment neural probe array of the invention. The neural probe array sensor is formed on a substrate 100. In other embodiments, the substrate 100 itself includes integrated electronics, as the temperature budget for forming the nanowire arrays of the invention is friendly to CMOS integrated circuits. An interface 102 (a metal alloy between the metal and the semiconductor due to the solid state reaction) serves as the base for vertical nanowire probes 103 and sets the center-to-center distance 104 of the vertical nanowire probes 103. The interface 102 is slightly larger in area than a base of the semiconductor probes 103 to provide enough mechanical support, and to tolerate alignment offsets within the limits of the lithography process. The interface 102 is a metal alloy that interfaces the semiconductor probe 103 with a metal contact 108, which together have enough mechanical strength to be tolerant to cell micromotion during measurements. The interface is an interface metal-semiconductor alloyed layer, e.g., a compound NiSi for Si nanowires reacted with Ni metal. Probes 103 are electrically conducted through individual and electrically isolated ones of the metal contacts 108, corresponding metal leads 110, and corresponding peripheral metal pads 112 (not shown in FIG. 1B, which is a partial view for clarity) for connection to a measurement circuit. Those metal connections, 108, 110 and 112, can be made of the same metal or different metals, and are patterned by photolithography or EBL (electron beam lithography) depending on their feature sizes. The probes 103 are a semiconductor material, e.g. silicon. The substrate 100 can be formed from a variety of materials, e.g. glass, sapphire, $SiO_2$/Si, etc. The probes 103 and metal connections can be formed in linear patterns, rectangular patterns, circular patterns, and a wide variety of other patterns. Fabrication processes of the invention do not limit the possible patterns beyond any limits of the CMOS compatible fabrication steps that are used. In preferred embodiments, the probes 103 consist of crystalline Si. The arrays of probes 103 can be tens, hundreds, thousands or tens of thousands of probes. Densities can be very high, while the probe size can be very fine. In example preferred embodiments, the semiconductor probes 100 have a diameter of ~10 nm-200 nm, and a height of ~5 µm-10 µm, though at the 10 nm diameter, the height may be reduced below ~5 µm. The probe center-to-center distance 104 can vary from submicron to tens of microns or hundreds of microns depending on the measurement requirements. The range of ~100 µm-200 µm is a preferred range to provide cells spacing to form healthy networks.

Figure 2B:
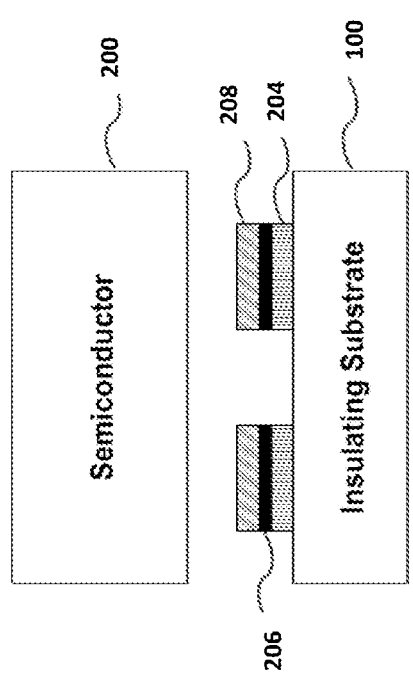

FIGS. 2A and 2B illustrate steps in a preferred fabrication method that integrate a semiconductor layer 200 onto the substrate 100. The semiconductor material 200 provides the material to form the vertical nanowire probe electrodes 103 in FIGS. 1A-1C. In FIG. 2A, a metal pattern has been formed on the substrate 100. The pattern includes three conductive metal layers 204, 206, 208. The pattern can be established via photolithography or EBL. The semiconductor layer thin layer 200 is then brought into contact with the metal layer 208, and the wafer bonding is then performed by a mild heat treatment (e.g., 400° C.~450° C.) under a compressive pressure (around 10 MPa) in a vacuum chamber with forming gas (5% $H_2$ in $N_2$) flow. 400° C. was chosen because it led to reacted NiSi leads that formed ohmic-like contacts with the heavily doped Si. This wafer bonding process takes advantage of the solid-state reaction between semiconductor layer 200 and the topmost metal layer 208, forming a stable metal-semiconductor alloy (as the interface 102) that will provide enough mechanical strength for the bonding. In preferred embodiments, the multi-layer metal pattern includes the different metal layers, 204, 206 and 208 that serve different functions, while also providing the interface 102, and metal pattern formed of the contacts 106, leads 110 and pads 112 of FIGS. 1A-1C. The base metal layer 204 promotes adhesion with the substrate 100, and has sufficient thickness to reduce the overall resistance of metal leads and interconnects. The center layer 206 is a diffusion blocking layer that allows only the solid-state reaction between the semiconductor 200 and the top metal layer 208 without allowing an alloy forming reaction with the blocking layer 206 or the base layer 204.

The bonding of FIGS. 2A-2B provides both bonding and fusion of a thin (~50 µm) Si substrate to the underlying host substrate, and embedding of electrical leads underneath active or passive Si components in the bonded substrate with low contact resistance. The integration technique is general to any other substrate that can sustain the NiSi reaction temperature (starts at 300° C.), including complementary metal oxide semiconductor (CMOS) integrated circuits and advanced planar and out of plane device geometries. See, e.g. X. Dai, B.-M. Nguyen, Y. Hwang, C. Soci, and S. A. Dayeh, "Novel Heterogeneous Integration Technology of III-V Layers and InGaAs FinFETs to Silicon," *Advanced Functional Materials* 24, 4420-4426, 2014; R. Chen, and S. A. Dayeh, "Size and Orientation Effects on the Kinetics and Structure of Nickelide Contacts to InGaAs Fin Structures," *Nano Letters* 15, 3770-3779. 2015. In experiments demonstrating the process of FIGS. 2A-2B, a thin Si chip, 5 mm×5 mm×50 µm brought into contact with the metal leads on the sapphire substrate, a moderate heat treatment (400° C.) and compressive pressure (around 10 MPa) in a vacuum chamber with forming gas ($H_2$ 5% in $N_2$) flow initiates a diffusion reaction between Ni and Si. Crystalline bonding interfaces were obtained. Similar bonding structure, morphology, and interfaces were validated on $SiO_2$/Si substrates to illustrate the versatility of the bonding steps.

Figure 3A:
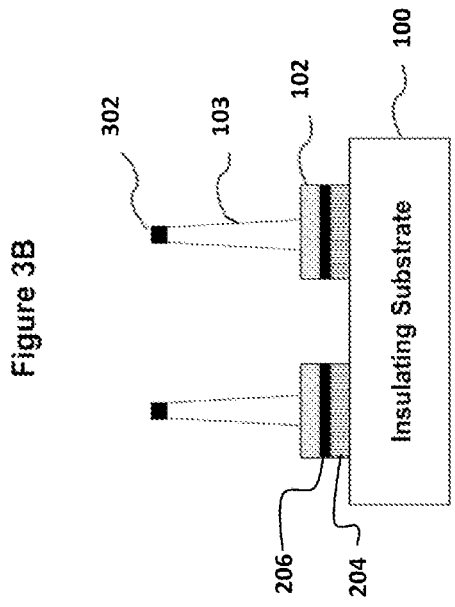
FIGS. 3A and 3B are schematic cross-sectional views of sequential steps for fabricating vertical nanowires with masked dry etching process in a preferred method for fabricating a neural probe sensor array in accordance with the invention.
Figure 3B:
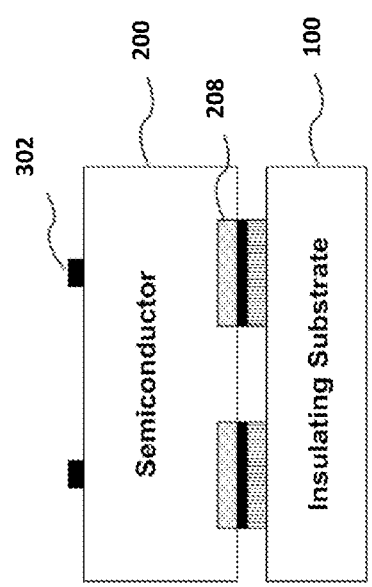

FIGS. 3A and 3B illustrate steps in a preferred fabrication method for forming the aligned vertical nanowire probes 103. The vertical nanowire probes 103 are fabricated by a masked dry etching process. A metal etching mask 302 is first defined on top of the semiconductor layer 200 by EBL with well-aligned location regarding the underneath metal connections 208 that form the metal ally interface via the FIGS. 2A-2B process. The alignment between photolithography and EBL can be achieved with the alignment makers defined near the peripheral of the substrate 100 (the peripheral portion can be left exposed, uncovered with dielectric), and similar alignment is also required for patterning the metal etching mask 302. An inductively coupled plasma (ICP) and reactive ion etching (RIE) based etching process then follows to remove all the semiconductor layer except for the area underneath the metal mask 302, so the vertical semiconductor probes 103 will be formed from the alloy base 102 and provide strong mechanical stiffness and good mechanical connection through the metal layers 206 and 204 to the substrate 100, as well as electrical connection to the layers 206 and 204. The alloyed layer 208/102 can withstand the dry etching process, and the etched vertical nanowire probe 103 has a diameter smaller than 200 nm and a height generally in between 5 μm-10 μm. The diameter of the vertical nanowire probe 103 is defined by the size of metal mask 302, and the height is determined by the semiconductor layer thickness that can be etched to a desired thickness by a similar ICP/RIE process after the wafer-bonding step but prior to mask patterning. The metal mask 302 can remain on the probes 103 to form a metal tip to the probes, as the metal is non-toxic to cells. Alternatively, it can also be removed. Experiments used an $SF_6/C_4F_8$ based ICP/RIE process is used to etch the Si everywhere except regions masked by the Ni dots, leaving vertically standing Si nanowires on NiSi leads.

Figure 4B:
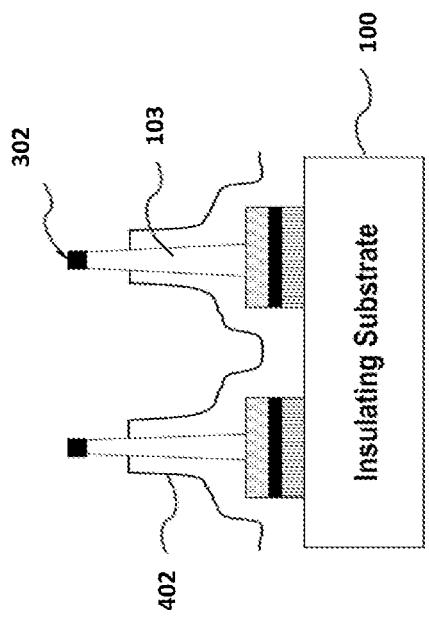
FIGS. 4A and 4B are schematic cross-sectional views of sequential steps showing the passivation of vertical nanowires with dielectric layer and in a preferred method for fabricating a neural probe sensor array in accordance with the invention.
Figure 4A:
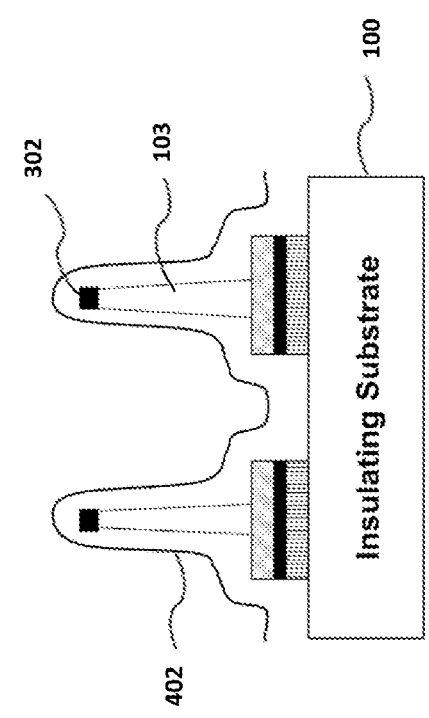

FIGS. 4A and 4B illustrate steps of a preferred method for insulating the metal leads and optionally stem portions of the vertical nanowire probes 103. A thin dielectric layer 402 is formed over the entire array include probes 103, metal pattern (contacts 108 and leads 110) and the substrate 100 to prevent signal cross-talk between adjacent electrodes 103. Through a spin coating of protective polymer layer, the base of dielectric layer 402 is protected and dielectric is removed from at least a tip portion of the vertical nanowire probes via a wet etching. Hence, the dielectric layer 402 covers the whole area of metal connections and leads and exposes at least a tip of each vertical nanowire probe 103, enabling the signal recording from each individual vertical nanowire probe 103 while isolating the probes from each other and from crosstalk/noise of the metal connections. Transmission electron microscopy (TEM) and elemental mapping by energy-dispersive X-ray spectroscopy (EDX) of the Si nanowires demonstrated crystalline structures and interfaces and highlight the usefulness of each layer: Si constitutes the main body of the sensor, $SiO_2$ constitutes the passivation outermost cylinder around the bottom portion of the nanowire, Ni is used for silicidation bonding and as a current conduction layer, and Ti is used as a Ni diffusion barrier and adhesion layer.

FIG. 5 is the overall process flow of a preferred method in accordance with FIGS. 2A-4B. A substrate is provided 500. Metal connections are patterned 501, which is reflected in FIG. 2A, which is followed by bonding 502, which is reflect in FIG. 2B. After the bonding, the semiconductor wafer can optionally be thinned 503 to a predetermined thickness that will set the vertical height of the vertical nanowire probes. The metal patterning mask is defined 504, as reflected in FIG. 3A and then dry etching is conducted 505 to form the vertical nanowire probe, as shown in FIG. 3B. Passivation is conducted 506, as shown in FIGS. 4A and 4B. Then the neural probe array is reach for conducting neural measurements.

Experiments were conducted and have demonstrated the preferred fabrication methods for high-density vertical semiconductor (Si) NEAs on insulating substrate (sapphire) for intracellular neural probes with individual electrode addressability. The experimental results are discussed, while artisans will recognize broader aspects of the invention from the experimental results. For example, other metal/semiconductor combinations can be used and the temperature adjusted so that the alloy forms to provide the interface alloy 102. NiSi is preferred as it provides one of the lowest processing temperatures for forming silicides in a solid-state form.

Figures 6A, 6B, 6C:
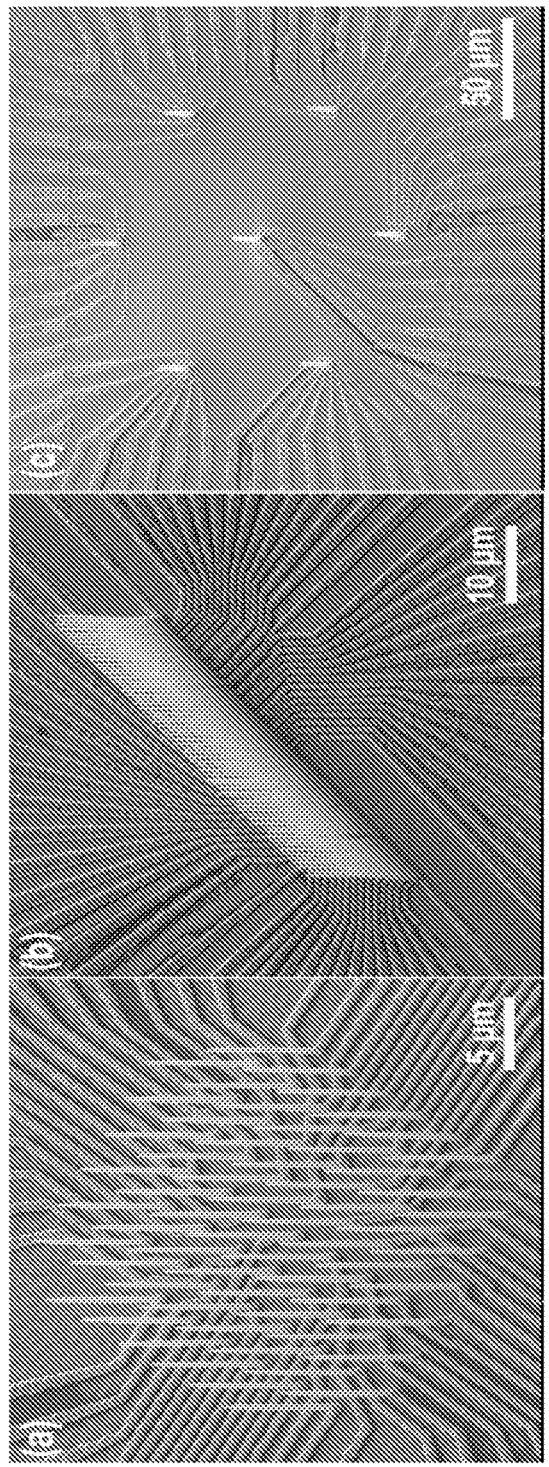
FIGS. 6A-6C are scanning electron microscope (SEM) images of example experimental neural probe sensor arrays of the invention fabricated in Si on a sapphire substrate with respective square, linear, and network shaped layouts.

Si neural probe arrays were fabricated a sapphire substrate with three different layout designs, which are shown in FIG. 6A-6C. The respective patterns were square, linear, and network shaped layouts. To achieve those structures, metal leads were first patterned on the sapphire substrate utilizing photolithography (for peripheral large pads) and EBL (for the fine center parts), followed by e-beam deposition of four metal layers, Ti/Ni/Ti/Ni (from base to top). The topmost Ni layer is around 200 nm and used for bonding with the Si thin layer via formation of a thin layer of Si—Ni alloy. This alloy was observed via high resolution transmission electron microscopy to have crystalline structure, and the crystalline structure of the bottom of the silicon electrode probe was also maintained. The Ti layer (50 nm) in between two Ni layers is used to block the Ni diffusion and reaction between Si and the lowermost Ni layer, providing enough conductance of the charge current carrying metal leads. The base Ti layer promotes the adhesion with sapphire substrate. Then, a 50 μm thick Si piece is brought in contact with this wafer, and the bonding is achieved with applied pressure and heating (~450° C.) benefitting from the solid-state reaction between Si and Ni electrodes to form the low-resistivity NiSi bonded interfaces. Following by an inductive coupled plasma/reactive ion etching (ICP/RIE) thinning process of Si to a designed thickness (8 μm in the experimental examples), Ni masks are patterned atop the Si piece with precisely controlled locations by EBL and ICP/RIE etching is used to fabricate the nanowires atop the NiSi leads. A large flexibility in the design and fabrication of various NEA layouts can be achieved by utilizing EBL to pattern the base electrodes and the Ni masks for fixing the Si nanowire position. The square NEAs (FIG. 6A) provide high spatial resolution to record and spatially map neuronal potential in single cells both intra- and extra-cellular. Linear NEAs (FIG. 6B) provide the platform to capture subthreshold and action potential generation and propagation in synapses, somas, and along dendritic and axonal peripheries during neuronal activity. Network NEAs (FIG. 6C) have the potential to map the interaction between neurons. FIGS. 7A-7B are high resolution images of individual vertical nanowire probes, before and after passivation, and FIG. 7C shows the square, high density array in a magnification that reveals the exposed tips and passivation details.

In the experiments, the 3D vertical nanowire probes were passivated by dielectric layer at the base and stem portion while with the tip was exposed for direct electrochemical interactions (through Faradaic redox reactions or through capacitive dipole screening) with ionic currents during cellular activity. 200 nm $SiO_2$ is first deposited all over the substrate. Then, PMMA is spin coated on the device, introducing a uniform thickness ~300 nm covering the base of each vertical wire while a thinner layer covers the wire sidewalls. A short $O_2$ plasma step is introduced to etch the PMMA at the tip of each vertical wire, and a diluted BOE etch step is then used to remove the $SiO_2$ layer at the exposed tip areas where the remainder of the $SiO_2$ layer remains protected with the thicker PMMA that covers the base of the NEAs. Finally, all the PMMA residue will be removed by $O_2$ plasma cleaning FIG. 8A is a photography of an example neural probe sensor array in accordance with the invention with Ni electrodes on a sapphire substrate. The substrate was then bonded to a PCB (printed circuit board) as shown in FIG. 8B via conductive epoxy, which allows the peripheral 64 electrodes to be connected to an analysis system, such as System 3® from Tucker-Davis Technologies. FIG. 8C is a microscope image of cultured pyramidal neurons from CA1 and CA3 of mouse hippocampus on the FIG. 8B chip with sensor array, FIG. 8D is data of recorded potentials from typical experimental neural probe sensor arrays of the invention showing positive (top) and negative (bottom) signals at the same time measured at separate electrodes, indicating potentially intra-(top) and extra-(bottom) cellular recording. The vertical nanowire probes were pre-treated with poly-D-lysine for cell plating and conventional cell culture techniques were then followed. A System 3® from Tucker-Davis Technologies was used for recordings, where the samples at day 7 post culture were loaded to Faraday cage to minimize the baseline of noise down to ~40-60 µV peak-to-peak. We recorded large positive potentials (up to 43 mV) on some channels. The recorded potential range on all channels ranged from ~0.2 mV-43 mV. The largest measured potentials here are typical of intra-cellular recordings, higher than that previously achieved in any nanoscale technology and close to that measured with patch-clamp techniques. Of note is that we didn't use electroporation in our experiments to obtain the large potentials. We hypothesize that the flexibility in our fabrication procedure that allows the realization of 3-4 times taller nanowires compared to previous art contributed to the natural internalization of the nanowires inside the cells. Additionally, for both intracellular and extracellular measurements, we were able to measure potential fluctuations that are similar to subthreshold potentials that are usually measured with patch clamp. These potential fluctuations are as large as 10-100 times the noise level and are not coupled from nearby channels. Furthermore, even in the extracellular configuration, our measured potentials were as large as 10 mV, significantly higher than what has been measured with planar electrodes and similar to that measured with nanowire/nanotube electrodes but with electroporation to access the inner potentials of the cells. These results indicate that performance that high-density nanoscale probes of the invention can deliver. The magnitude of the sensed potentials is typical of intra-cellular recordings, higher than that previously achieved in any nanoscale technology known to the inventors and close to that measured with patch-clamp techniques. The neural probe array is also compatible with existing neurophysiology stations including Multichannel Systems (http://www.multichannelsystems.com/), TDT (http://www.tdt.com/), etc.

Experimental arrays demonstrated a high packing density of 6.25 Million/$cm^2$ at a pitch of 4 µm. Experimental devices also demonstrated sub-micrometer pitch at a site-to-site spacing of 750 nm. The array geometry can be tailored for the optimal growth of neuronal networks that are interconnected with sealed microfluidic channels that can allow growth of neurites and synaptic connections but prevent cell-body plating inside the channels. The electrochemical impedance in all of these configurations is relatively uniform and validated a capacitive dominant coupling behavior with neuronal activity.

Figure 9A:
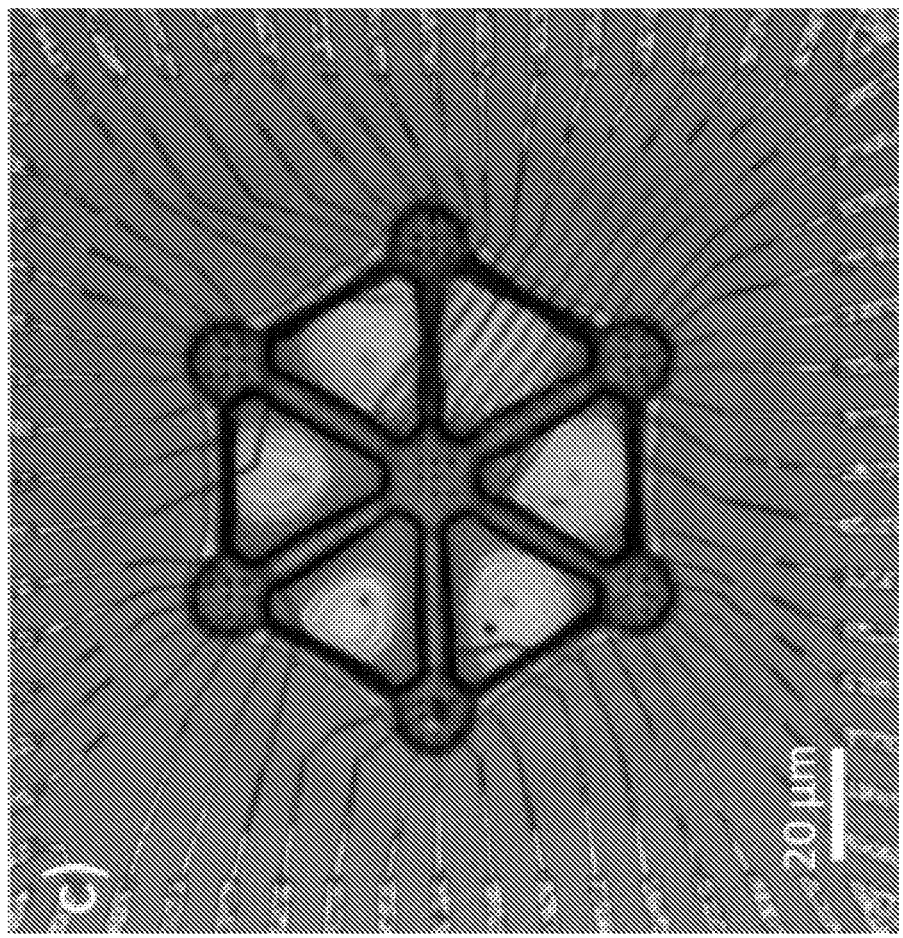
FIG. 9A is an image of a neural probe array including a microfluidic network for neuron cells.
Figure 9B:
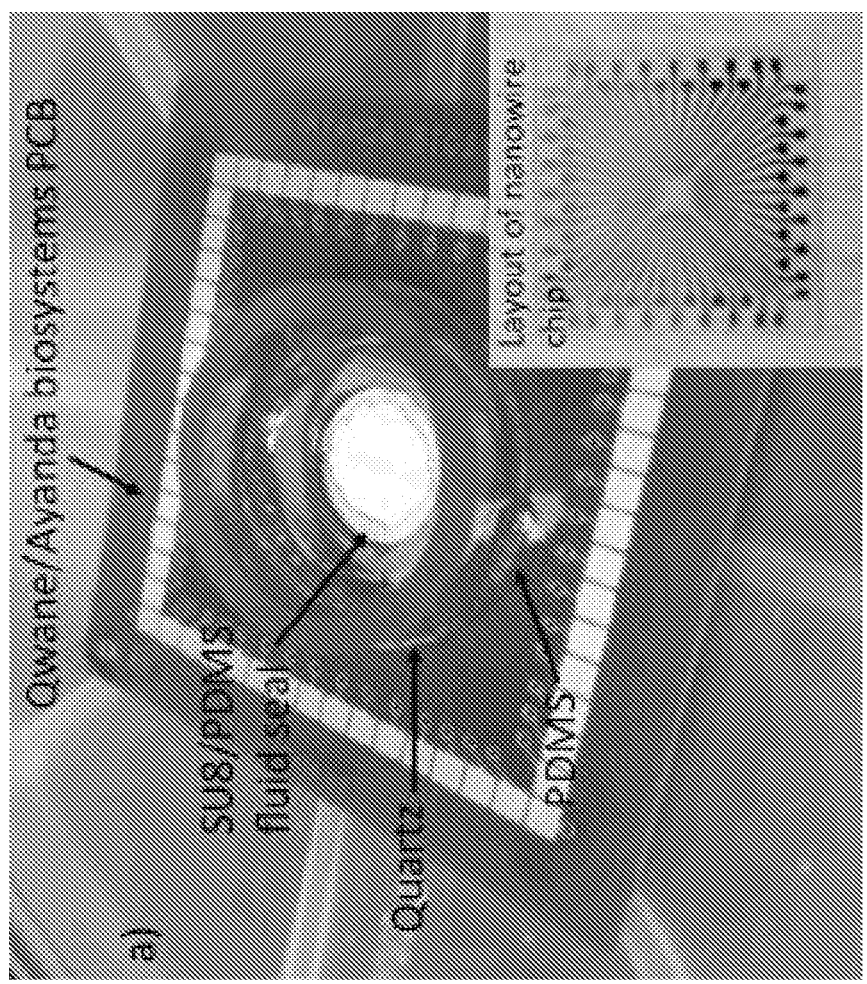
FIG. 9B shows an example neural probe arrays packaged in SU8.

FIGS. 9A-9B show neural electrode probe arrays packaged in a sealed fluid network. In FIG. 9A, neuron plating regions and microchannels were sealed with SU8 with optimized processing conditions to seal a microfluidic channel in SU8 that connects the vortices of the hexagon and yet maintains a sealed top to prevent neuron plating in these microfluidic channels.

Figure 10:
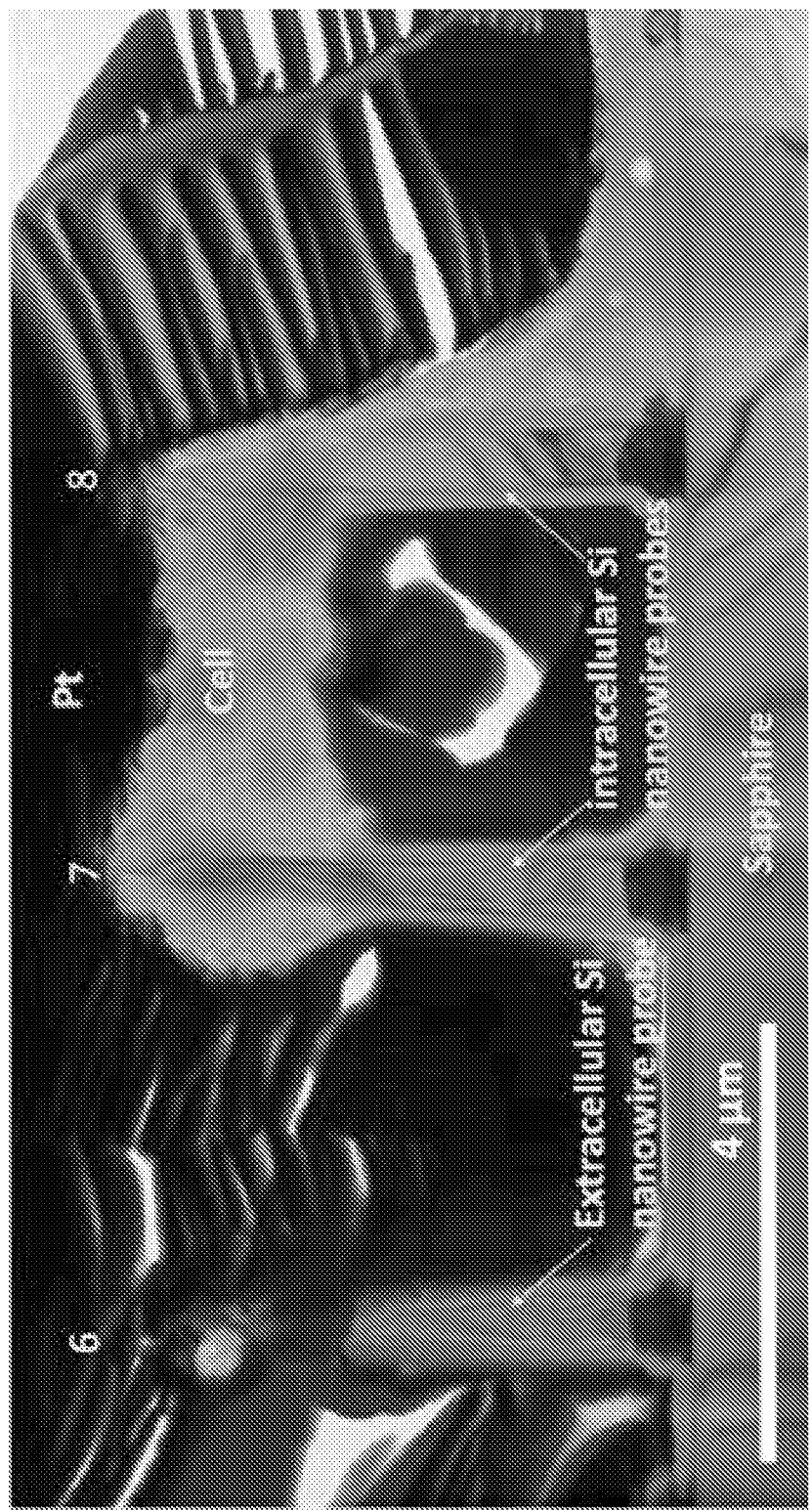
FIG. 10 is a transmission electron microscopy (TEM) image of an experimental vertical nanowire probes involved in an example intracellular and extracellular measurement.

The FIG. 9B structure was used to test biological interfaces established between Si vertical nanowire probes and neurons and the resulting recorded electrophysiological activity. We tested feasibility for electrophysiology and pharmacology using mouse hippocampal and human iPSC-derived neurons. For both primary and hiPSC-derived neurons, we found strong interaction between neurons and vertical probe electrodes characterized by cell outgrowth and engulfment to the vertical Si nanowires. The cell-electrode interface was generally established in two different configurations that were validated with TEM: intracellular, where the NW electrode permeates the cell giving recording access to potential changes within and extracellular, where the cell engulfs the NW electrode providing sufficient coupling between the cell and the electrode to enable high fidelity extracellular recordings. FIG. 10 shows vertical nanowire probes involved in an example intracellular and extracellular measurement.

Figure 11:
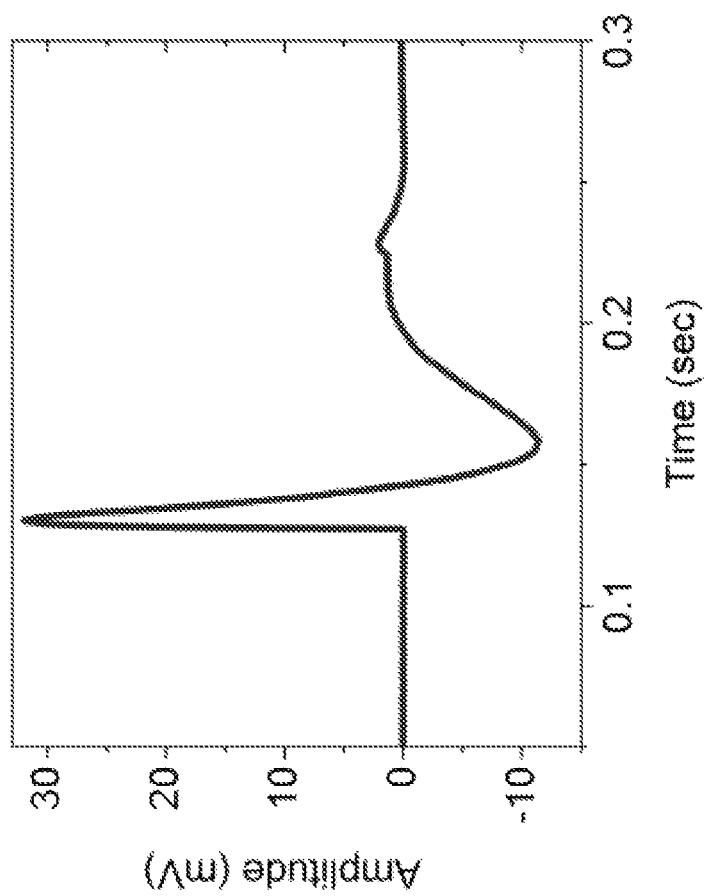
FIG. 11 is data recorded from a mouse hippocampal neuron including a measured potential of 43 mV.

Measurements recorded oscillatory potentials that are signatures of subthreshold oscillations and large action potentials that in some cases reached 43 mV. FIG. 11 shows data of this example highest measurement recorded from a mouse hippocampal neuron. To the knowledge of the inventors intracellular measured potentials in experiments with a neural probe array of the invention are the largest potentials ever measured using a nanoscale probe technology interfaced with cultured neurons and the detected extracellular potentials are one to two orders of magnitude larger than the typical values reported in the literature. In addition, physiological measurements on mouse hippocampal neurons cultured for 8 days on our platform displayed small potential fluctuations prior to the firing event in the intracellular and the extracellular contact configurations. To the best of our knowledge, this is the first clear experimental measure of spontaneous subthreshold activity in neurons using nanowires, which demonstrates an essential capability for decoding individual neuronal cell activity in a large network of neurons using sub-cellular scalable sensors. Pharmacological stimulation and inhibition validated the physiological origin of the measured potentials. With glutamate injection, we observed an increase of the cell activity with respect to frequency and amplitude when compared to the baseline spontaneous activity measured on the same channel. The injection of tetrodotoxin (TTX) inhibited the activity on the same channel. Similarly, for the extracellular configuration, the injection of KCl led to increased activity relative to the baseline recording which was also eliminated by TTX treatment.

Figure 12:
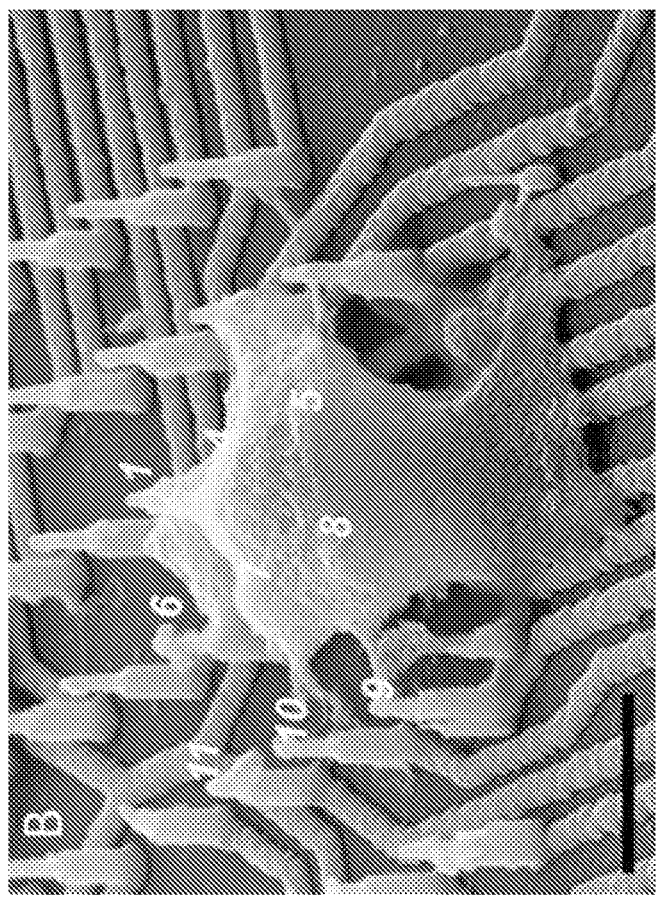
FIG. 12 is an SEM image of a human iPSC cell that encompasses multiple vertical nanowire probes in an experimental array and neurite outgrowth to additional probes.

The sensitivity of the present neural probe array was also demonstrated with electrically active hiPS C-derived neurons to show that the present arrays will be useful for mapping activity from human brain cells or screening drugs for neurological diseases. Human iPSC-derived cortical neurons cultured on our platform exhibited large cell bodies that overlapped with multiple nanowires. FIG. 12 shows a human iPSC cell that encompasses multiple vertical nanowire probes and neurite outgrowth to additional probes. Measured potentials for nanowire channels that corresponded to contacted probes at two different times $t_1$ and $t_2$ showed significant potentials while other channels displayed either no activity or very weakly coupled potentials. Nanowires 7 & 8 displayed positive action potentials whereas nanowire 6 displayed a negative action potential. From the SEM image of FIG. 12, one can note the extracellular nature of the interface with nanowire 6. To uncover the nature of the interface with nanowires 7 & 8, we performed a sequential focused ion beam (FIB) cut and thinning of a 300-400 nm slice on the sample in regions of wires marked 6, 7, and 8 post Pt plating. The sample was thin enough to allow electron transmission for TEM characterization without risking significant damage to the cell body during the FIB milling process. SEM images of the FIB slice showed a clear dark contrast of the cell around nanowires 7 & 8 showing an intimate contact between the nanowires and the iPSC cells. Because the action potentials measured with wires 7&8 were positive and that with wire 6 was negative, we concluded that positive action potentials measured by the experimental vertical probe array are likely to be intracellular potentials.

Such measurement of subthreshold activity using the present nanowire neural vertical nanowire probes from human neurons opens new prospects for mapping neuronal activity in large networks. Given the scalability of the present neural probe arrays, the simultaneous recording of minute changes in cell potentials can uncover details on the synthesis, processing, and execution of neuronal network activity. In vitro, highly parallel drug screening experiments can be performed without the need of the laborious non-scalable patch-clamp. In vivo, targeted modulation of individual neural circuits or even single cells within a network becomes possible, and implications for bridging or repairing networks in neurologically affected regions becomes within reach. Overall, neural probe arrays of the invention can greatly enhance both in vivo and in vitro applications, as will be appreciated by artisans.

Figure 13:
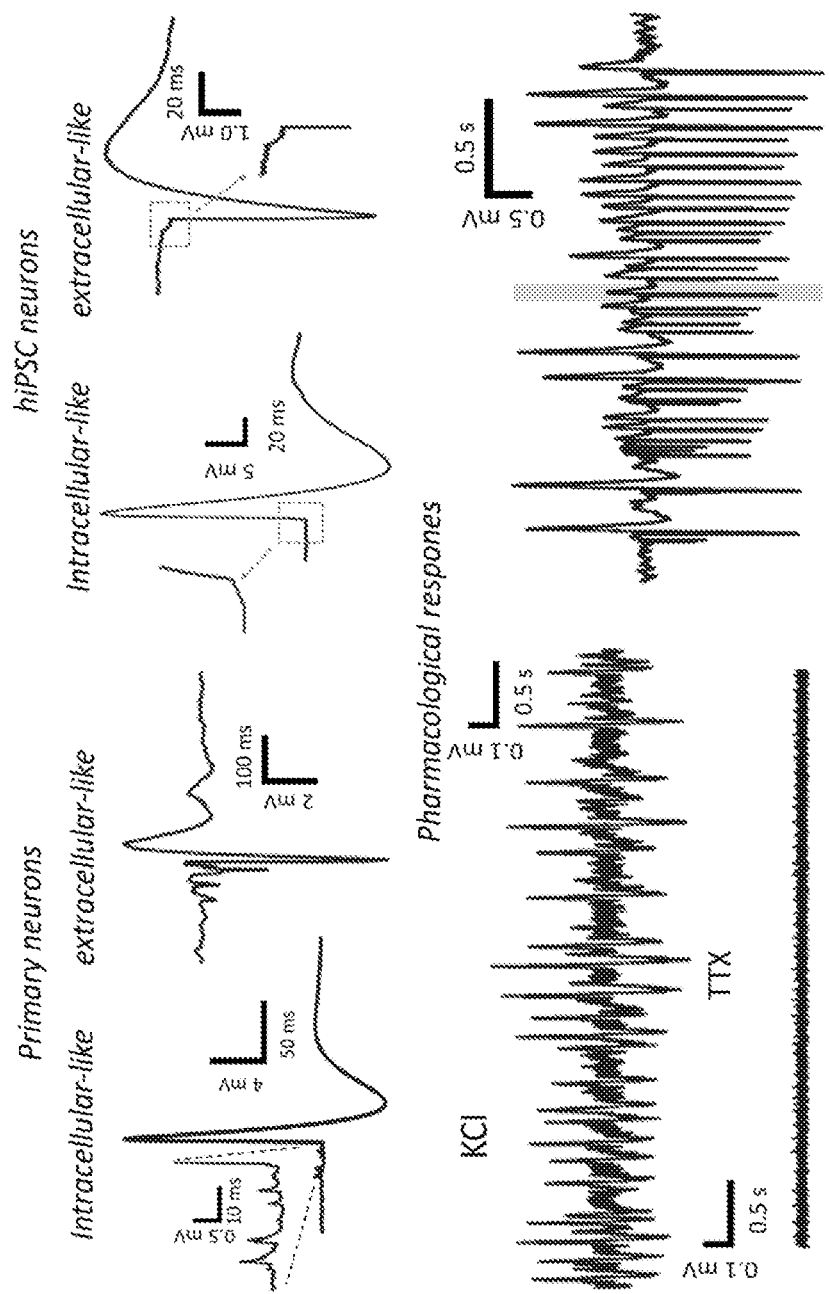
FIG. 13 provides pharmacological response data for intracellular and extracellular measurements with an experimental array.

Pharmacological response was also tested, and the results shown in FIG. 13. FIG. 13 data was taken upon injection of neurostimulants such as glutamate and KCl, the cellular activity for both intracellular and extracellular neuronal spiking increased and with neuroinhibitant such as neurotoxin, neuronal spiking vanished. This validated the pharmacological response of an experimental nanowire array. Demonstration of pharmacological response of nanowire platform: Spontaneous measured action potentials recording from primary and hiPSC neurons. A 13.2 mM KCl injection increased firing rate and 0.93 µM TTX eliminated firing for both intra and extracellular like configurations demonstrating on both primary and iPSC neurons.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A neural probe sensor array comprising:
a substrate;
a metal pattern comprising a plurality of electrically isolated metal contacts disposed on the substrate;
a plurality of semiconductor vertical nanowire probes, wherein each of the plurality of semiconductor vertical nanowire probes are disposed on a corresponding electrically isolated metal contact of the plurality of electrically isolated metal contacts; and
a dielectric coating covering the metal pattern and lower portions of the plurality of semiconductor vertical nanowire probes while leaving tip portions of the vertical nanowire probes exposed such that each of the plurality of semiconductor vertical nanowire probes is individually electrically addressable.

2. The neural probe sensor array of claim 1, wherein said plurality of semiconductor vertical nanowire probes each have a diameter of about 10 nm-200 nm, and a height of about 5 µm -10 µm.

3. The neural probe sensor array of claim 2, wherein said dielectric coating covers base and stem portions of each of said plurality of semiconductor vertical nanowire probes leaving the tip portions exposed, and the tip portions are approximately ⅓ the length of said plurality of semiconductor vertical nanowire probes.

4. The neural probe sensor array of claim 1, wherein the tip portions are formed from a metal.

5. The neural probe sensor array of claim 1, comprising a semiconductor-metal alloy interfacing said plurality of semiconductor vertical nanowire probes to said plurality of electrically isolated metal contacts of said metal pattern.

6. The neural probe sensor array of claim 1, wherein said electrically isolated metal contacts are connected to corresponding individual metal leads extending from the individual electrically isolated metal contacts, and corresponding peripheral metal pads for connection to a measurement circuit.

7. The neural probe sensor array of claim 1, wherein the center-to-center distance between individual ones of said plurality of semiconductor vertical nanowire probes is in a range of less than one micron to tens of microns.

8. The neural probe sensor array of claim 7, wherein the center-to-center distance is about 750 nm.

9. The neural probe sensor array of claim 1, wherein said plurality of semiconductor vertical nanowire probes have a packing density of 6.25Million/cm2 at a pitch of 4 µm.

10. The neural probe sensor array of claim 1, wherein said plurality of semiconductor vertical nanowire probes comprises tens to thousands of individual semiconductor vertical nanowire probes all isolated from each other.

11. The neural probe sensor array of claim 1, wherein said plurality of semiconductor vertical nanowire probes are arranged in one of a linear pattern, a rectangular pattern, or a network pattern.

12. The neural probe sensor array of claim 1, wherein said substrate comprises one of glass, sapphire, an integrated circuit and SiO2/Si.

13. The neural probe sensor array of claim 1, wherein said plurality of semiconductor vertical nanowire probes consist of crystalline Si.

14. The neural probe sensor array of claim 1, further comprising packaging for sealing fluid and cells into contact with the sensor array.

15. The neural probe sensor array of claim 1, wherein said plurality of semiconductor vertical nanowire probes comprises at least hundreds of individual semiconductor vertical nanowire probes all isolated from each other.

16. The neural probe sensor array of claim 15, wherein said plurality of semiconductor vertical nanowire probes comprises at least thousands of individual semiconductor vertical nanowire probes all isolated from each other.

17. The neural probe sensor array of claim 16, wherein said plurality of semiconductor vertical nanowire probes comprises at least tens of thousands of individual semiconductor vertical nanowire probes all isolated from each other.

18. The neural probe sensor array of claim 11, wherein said plurality of semiconductor vertical nanowire probes are arranged in a rectangular pattern.

19. The neural probe sensor array of claim 11, wherein said plurality of semiconductor vertical nanowire probes are arranged in a network pattern.

20. The neural probe sensor array of claim 1, wherein said substrate comprises an integrated circuit.

* * * * *